(12) United States Patent
Hirakawa et al.

(10) Patent No.: US 12,357,875 B2
(45) Date of Patent: Jul. 15, 2025

(54) EXERCISE ANALYSIS DEVICE, EXERCISE ANALYSIS METHOD, AND EXERCISE ANALYSIS PROGRAM

(71) Applicant: ASICS CORPORATION, Kobe (JP)

(72) Inventors: Nao Hirakawa, Hyogo (JP); Yasuhiro Nomura, Hyogo (JP); Hajime Kumami, Hyogo (JP)

(73) Assignee: ASICS CORPORATION, Kobe (JP)

( * ) Notice: Subject to any disclaimer, the term of this patent is extended or adjusted under 35 U.S.C. 154(b) by 136 days.

(21) Appl. No.: 18/044,796

(22) PCT Filed: Oct. 20, 2020

(86) PCT No.: PCT/JP2020/039391
§ 371 (c)(1),
(2) Date: Mar. 10, 2023

(87) PCT Pub. No.: WO2022/085070
PCT Pub. Date: Apr. 28, 2022

(65) Prior Publication Data
US 2023/0285803 A1    Sep. 14, 2023

(51) Int. Cl.
*A63B 24/00*     (2006.01)
*A63B 71/06*     (2006.01)

(52) U.S. Cl.
CPC ...... *A63B 24/0006* (2013.01); *A63B 24/0062* (2013.01); *A63B 24/0075* (2013.01); *A63B 71/0622* (2013.01); *A63B 2024/0009* (2013.01)

(58) Field of Classification Search
CPC ............ A63B 24/0006; A63B 24/0062; A63B 24/0075; A63B 71/0622;
(Continued)

(56) References Cited

U.S. PATENT DOCUMENTS 4,919,418 A * 4/1990 Miller .................. A63B 21/151
                                                                482/901
5,230,672 A * 7/1993 Brown ................. A63B 21/154
                                                                482/4
(Continued)

FOREIGN PATENT DOCUMENTS

JP    2015-154988 A    8/2015
JP    2016-034481 A    3/2016
(Continued)

OTHER PUBLICATIONS

The extended European search report issued by the European Patent Office on Sep. 4, 2023, which corresponds to European Patent Application No. 20958623.9-1113 and is related to U.S. Appl. No. 18/044,796.

(Continued)

*Primary Examiner* — Garrett K Atkinson
(74) *Attorney, Agent, or Firm* — Studebaker Brackett PLLC (57) ABSTRACT

An exercise analysis device includes: a group classification unit that classifies activity data, as which measurement data associated with an exercise motion is recorded together with certain reference data that changes during exercise, into multiple groups based on the reference data; a representative data generating unit that generates representative data for the activity data in each of the multiple groups; and a tendency analysis unit that analyzes a tendency of the representative data with respect to the reference data in the multiple groups. With the exercise analysis device, exercise motions can be analyzed appropriately in consideration of the tendency of the entire exercise.

10 Claims, 6 Drawing Sheets

(58) Field of Classification Search
CPC ............ A63B 2024/0009; A61B 5/112; A61B 5/1116; A61B 5/1123; A61B 5/7246; A61B 5/1121; A61B 5/1128; A61B 5/7267; A61B 5/1071; A61B 2560/0242; A61B 2562/0219; A61B 5/681; A61B 5/6898; A61B 5/7275; A61B 5/7435; A61B 5/1112; A61B 5/024; A61B 2503/10; A61B 2505/09; G06F 18/2321; G06F 18/27; G09B 19/0038; G16H 20/30; G16H 40/63; G16H 40/67; G16H 50/20; G06V 40/25
See application file for complete search history.

(56) References Cited

U.S. PATENT DOCUMENTS

| | | | | |
|---|---|---|---|---|
| 5,254,066 | A * | 10/1993 | Brown | A63B 24/0062 601/40 |
| 5,919,115 | A * | 7/1999 | Horowitz | A63B 21/00181 482/901 |
| 6,280,361 | B1 * | 8/2001 | Harvey | A63B 24/00 482/4 |
| 2004/0204257 | A1 * | 10/2004 | Boscha | A63B 60/42 473/131 |
| 2006/0029916 | A1 * | 2/2006 | Boscha | A63B 69/3614 434/252 |
| 2007/0265138 | A1 * | 11/2007 | Ashby | A63B 22/0235 482/8 |
| 2016/0029943 | A1 * | 2/2016 | Mizuochi | A61B 5/0022 600/595 |
| 2016/0133152 | A1 * | 5/2016 | Arif | A63B 24/0062 434/247 |
| 2017/0372482 | A1 * | 12/2017 | Yamagiwa | G06V 40/25 |
| 2018/0001181 | A1 * | 1/2018 | Von Prellwitz | A63B 24/0075 |
| 2018/0264306 | A1 * | 9/2018 | Agrawal | A63B 24/0087 |
| 2019/0009133 | A1 * | 1/2019 | Mettler May | G09B 19/0038 |

FOREIGN PATENT DOCUMENTS

| | | |
|---|---|---|
| JP | 2016-112053 A | 6/2016 |
| JP | 2017-000455 A | 1/2017 |
| JP | 2017-077403 A | 4/2017 |
| JP | 2019-181040 A | 10/2019 |
| JP | 2020-054913 A | 4/2020 |
| JP | 2020-113117 A | 7/2020 |
| KR | 10-2020-0116607 A | 10/2020 |

OTHER PUBLICATIONS

International Search Report issued in PCT/JP2020/039391; mailed Dec. 28, 2020.
International Preliminary Report on Patentability (Chapter I) and Written Opinion of the International Searching Authority issued in PCT/JP2020/039391; issued Apr. 13, 2023.

* cited by examiner

EXERCISE ANALYSIS DEVICE, EXERCISE ANALYSIS METHOD, AND EXERCISE ANALYSIS PROGRAM

TECHNICAL FIELD

The present invention relates to a technology for analyzing exercise motions.

BACKGROUND ART

In recent years, mobile communication terminals such as smartphones have been becoming more lightweight, and so-called wearable devices have been actively developed, as typified by smartwatches. These devices can be worn also during exercise, such as running, and can measure exercise motions with built-in acceleration sensors and the like. There are also services and applications that provide guidance for improving exercise motions based on the measurement results.

PRIOR ART REFERENCE

Patent Literature

Patent Literature 1: Japanese Unexamined Patent Application Publication No. 2015-154988

SUMMARY OF INVENTION

Technical Problem

Patent Literature 1 discloses a technology for reducing data transfer volume and speeding up exercise analysis processing by setting desired extraction conditions when transferring data measured by various devices during exercise, such as running and walking, to a server for exercise analysis. As examples of the extraction conditions, conditions based on distance, such as "every 1 km", those based on time, such as "every 5 minutes", and those based on pace changes, such as "when the pace deviates from a set pace range", and the like are disclosed. Thus, it is intended to perform efficient exercise analysis by setting an extraction condition that is considered to affect the user's exercise motions.

In the technology disclosed in Patent Literature 1, since only the measurement data that match the extraction condition are transferred to the server for exercise analysis, appropriate exercise analysis can be performed within the range of the extracted measurement data. However, it is not ensured that the results of the exercise analysis performed within such a limited range are also reasonable for the entire exercise that includes most of the measurement data that have not been extracted. In particular, there may be a case where extracted measurement data turns out to be abnormal data, for some reason, that is contrary to the tendency of the entire exercise, and the exercise analysis results in such a case may rather worsen the user's exercise motions.

The present invention has been made in view of such a situation, and a purpose thereof is to provide an exercise analysis device that can appropriately analyze exercise motions in consideration of the tendency of the entire exercise.

Solution to Problem

To solve the problem above, an exercise analysis device according to one aspect of the present invention includes: a group classification unit that classifies activity data, as which measurement data associated with an exercise motion is recorded together with certain reference data that changes during exercise, into multiple groups based on the reference data; a representative data generating unit that generates representative data for the activity data in each of the multiple groups; and a tendency analysis unit that analyzes a tendency of the representative data with respect to the reference data in the multiple groups.

According to this aspect, by classifying a series of activity data recorded during exercise into multiple groups and by analyzing the tendency of the representative data among the groups, the exercise motions can be appropriately analyzed in consideration of the tendency of the entire exercise.

Another aspect of the present invention relates to an exercise analysis method. The method includes: a group classification step of classifying activity data, as which measurement data associated with an exercise motion is recorded together with certain reference data that changes during exercise, into multiple groups based on the reference data; a representative data generating step of generating representative data for the activity data in each of the multiple groups; and a tendency analysis step of analyzing a tendency of the representative data with respect to the reference data in the multiple groups.

Optional combinations of the aforementioned constituting elements, and implementation of the present invention in the form of methods, apparatuses, systems, recording media, and computer programs may also be practiced as additional modes of the present invention.

Advantageous Effects of Invention

The present invention enables appropriate analysis of exercise motions in consideration of the tendency of the entire exercise.

DESCRIPTION OF EMBODIMENTS

In the present embodiment, analysis of exercise motions and guidance for improvement thereof is performed based on data measured during a user's exercise. When the exercise motions are analyzed, the measurement data are grouped based on reference data with regard to speed or the like. For example, the data are classified into three groups: a group of the case where the speed is within a normal range, a group of the case where the speed is greater than the normal range, and a group of the case where the speed is smaller than the normal range. In this case, the number of measurement data is smaller in the group with the speed greater or smaller than the normal range. However, by conducting analysis using representative data from each group, the tendency of each group can be precisely grasped regardless of the number of data included in each group.

Figure 1:
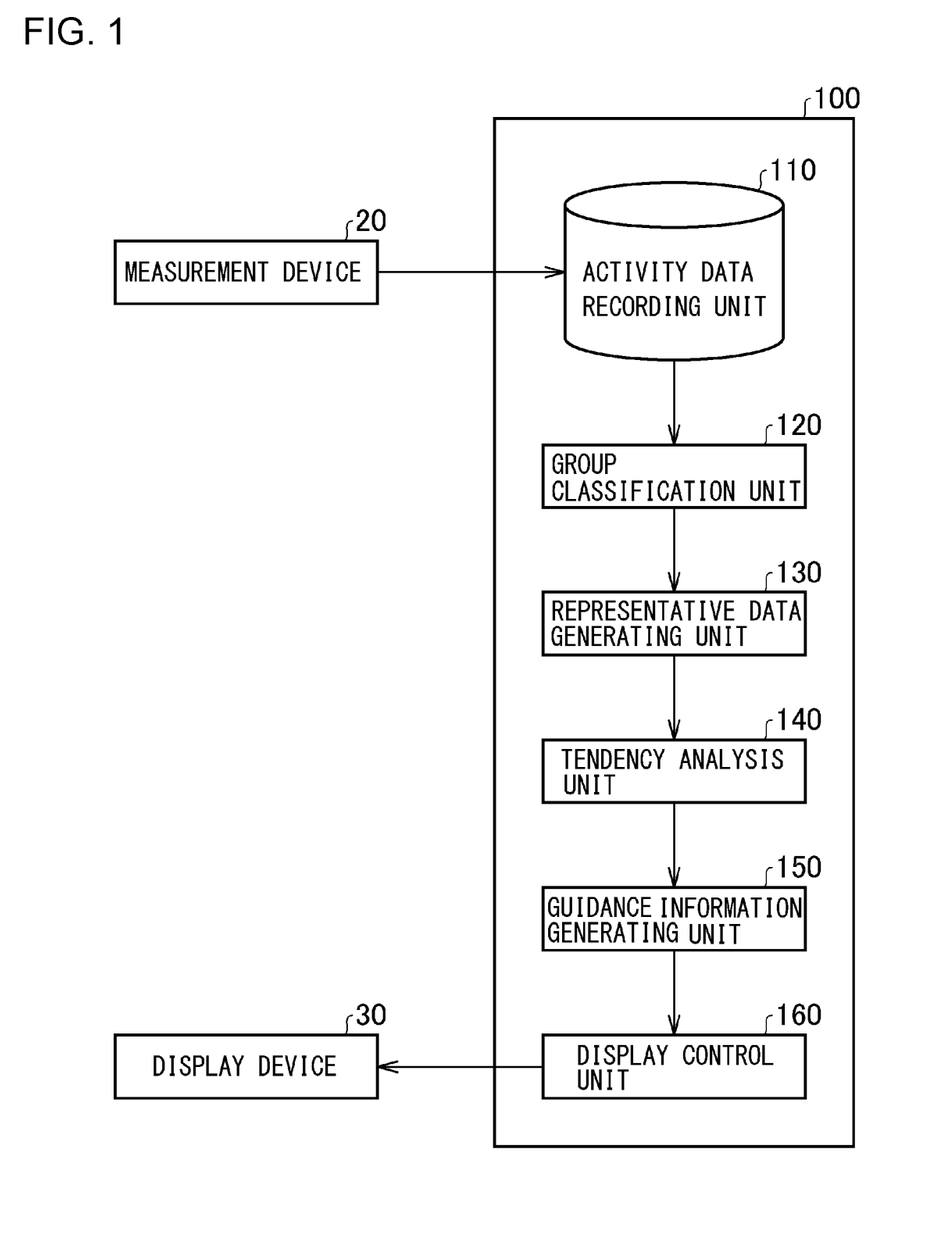
FIG. 1 is an overall configuration diagram of a system that includes an exercise analysis device according to an embodiment.

FIG. 1 is an overall configuration diagram of a system that includes an exercise analysis device 100 according to the embodiment. The exercise analysis device 100 analyzes exercise motions based on measurement data measured by a measurement device 20 while a user is running. The analysis result is displayed together with guidance information for improving the exercise motions, on a display device 30 used by the user.

The measurement device 20 may be a wearable device, such as a smartwatch, or a smartphone that can be worn by the user during running, for example, and measures exercise motions during running with a built-in sensor. However, the measurement device 20 in the present embodiment is not limited thereto and may be any device that has a data measurement function during running and a minimum data transmission function to transmit the measurement data to the exercise analysis device 100. For example, as the measurement device 20, a camera (an image capturing device) for capturing images of the user during running may be used. In this case, the data captured by the camera is provided as the measurement data to the exercise analysis device 100. In this way, since various devices can be used as the measurement device 20, the exercise analysis device 100 can acquire various measurement data associated with the user's exercise motions during running.

For example, when a wearable device or a smartphone is used as the measurement device 20 as described above, through an acceleration sensor, an angular velocity sensor, a position sensor (such as the GPS), a magnetic sensor, and the like built into the device, basic physical quantities associated with the user's position and the exercise performed by the user can be obtained as the measurement data. By combining such measurement data as appropriate and performing computation, not only basic information, such as the user's position, speed, and acceleration during running, but also biomechanical data on the details of the user's exercise motions, such as the user's posture, rotation angle of the waist or pelvis, vertical motions of the body's center of gravity, strength and angle of pushing off, pitch, stride, ground contact time, position and angle of ground contact, spring modulus of the body, and landing impact, can be obtained. In addition, information regarding the running course, such as the distance, altitude, and gradient, can also be obtained.

Furthermore, when the measurement device 20 is equipped with a sensor that measures the external environment, such as an ambient light sensor that measures brightness and the like, a temperature sensor, and a humidity sensor, the exercise analysis device 100 can perform appropriate analysis also in consideration of the external environment during running. Also, when a wearable device capable of measuring biological signals, such as heartbeat, is used as the measurement device 20, which has been actively developed in recent years, the exercise analysis device 100 can perform appropriate analysis and guidance for improvement also in consideration of the user's physical condition.

The measurement device 20 need not necessarily be worn by the user during exercise and may measure the user during exercise from the surroundings. The image capturing by a camera as described previously is considered to be a typical example, but the device is not limited thereto. For example, when the user is running in a restricted indoor area using a treadmill or the like, the measurement device 20 that is difficult to carry can also be used, so that the variety of available measurement data is remarkably increased.

With regard to the various measurement devices 20 described with examples above, multiple measurement devices 20 may be used in a single exercise. For example, a wearable device as a first measurement device 20 may be worn by the user to perform measurement, and, at the same time, a camera as a second measurement device 20 may be used to capture images of the user. Based on the measurement data from such multiple measurement devices 20, the exercise analysis device 100 can analyze the user's exercise motions from multiple aspects and generate guidance information for effective improvement of the exercise motions.

The display device 30 is a device that displays the exercise analysis result and the guidance information for improving exercise motions, generated by the exercise analysis device 100 based on the measurement data from the measurement device 20. For example, when a smartphone is used as the measurement device 20, it also functions as the display device 30 that displays the analysis result and guidance information. Also, when a camera or the like that does not have a display function is used as the measurement device 20, another device owned by the user, such as a smartphone, tablet, watch, smart glass, or computer, is used as the display device 30.

The exercise analysis device 100 is configured on a server capable of communicating with the measurement device 20 and the display device 30 via a communication network. Also, data transfer between the exercise analysis device 100 and the measurement device 20 or display device may be performed via a portable storage medium, without the intervention of a communication network. The exercise analysis device 100 includes an activity data recording unit 110, a group classification unit 120, a representative data generating unit 130, a tendency analysis unit 140, a guidance information generating unit 150, and a display control unit 160.

The activity data recording unit 110 records, as activity data, measurement data associated with an exercise motion together with predetermined reference data that changes during exercise. The measurement data associated with an exercise motion here is an actual measured value of a parameter for which analysis and generation of guidance information is performed by the exercise analysis device 100. Such measurement data include, for example, the various biomechanical data mentioned above (such as the user's posture, rotation angle of the waist or pelvis, vertical motions of the body's center of gravity, strength and angle of pushing off, pitch, stride, ground contact time, position and angle of ground contact, spring modulus of the body, and landing impact). Also, the reference data is data used as a standard in group classification processing performed by the group classification unit 120 in a later stage and is measured during exercise in conjunction with the above-mentioned measurement data associated with an exercise motion. Examples of the reference data include time, the number of steps, distance, positions, speed, acceleration, altitude, gradients, luminance, temperature, humidity, and biological signals such as heartbeat, during exercise. Thus, the reference data is not limited to data that changes monotonically as the exercise proceeds, such as time, the number of steps, distance, and a position, and data that increases or decreases during exercise may also be used, such as speed, acceleration, altitude, a gradient, luminance, temperature, humidity, and heartbeat.

The activity data recording unit 110 records, as the activity data, the measurement data associated with an exercise motion as described above and the reference data that changes during exercise, related to each other as a pair. At the time, the activity data recording unit 110 can record the activity data over a single exercise or multiple exercises. As the simplest example, when each of the measurement data and the reference data is constituted by only one parameter, the activity data is represented as a point on an x-y plane in which the x-axis represents the reference data, and the y-axis represents the measurement data.

Figure 2A:
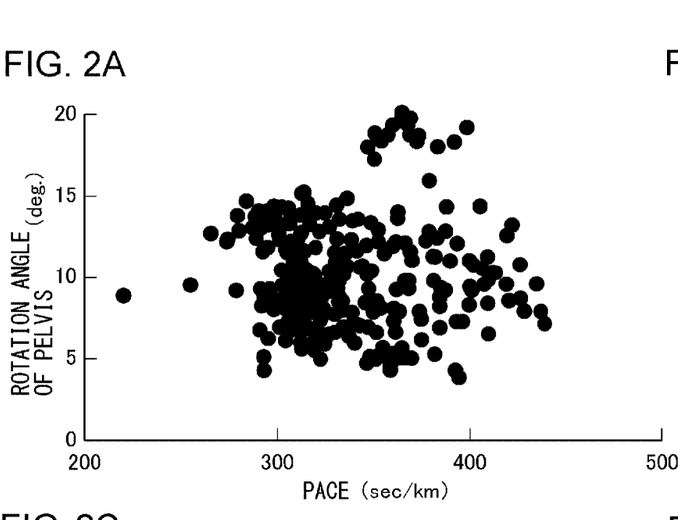
FIG. 2 show an example of activity data processed by the exercise analysis device.

FIG. 2A shows an example of recorded activity data in the case where the "pace" {the time required per unit distance (inverse of speed)} is selected as the reference data, and the "rotation angle of the pelvis" is selected as the measurement data. In this example, the activity data have been recorded over about 20 runs, and the x-axis as the horizontal axis represents the pace, and the y-axis as the vertical axis represents the rotation angle of the pelvis. As shown in FIG. 2A, a series of activity data recorded during exercise constitute a scatter diagram that includes points plotted in the coordinate space, with the reference data and measurement data employed as the coordinate axes.

When it is generalized, in the case where the measurement data is represented by n parameters (y1, y2, . . . , yn) and the reference data is represented by m parameters (x1, x2, . . . , xm), the activity data constitute a scatter diagram that includes points plotted in the m+n-dimensional coordinate space, with the m+n parameters employed as the coordinate axes. In the following, for the sake of simplicity, the present embodiment will describe the example of two dimensions (m, n=1) shown in FIG. 2A.

Figure 2B:
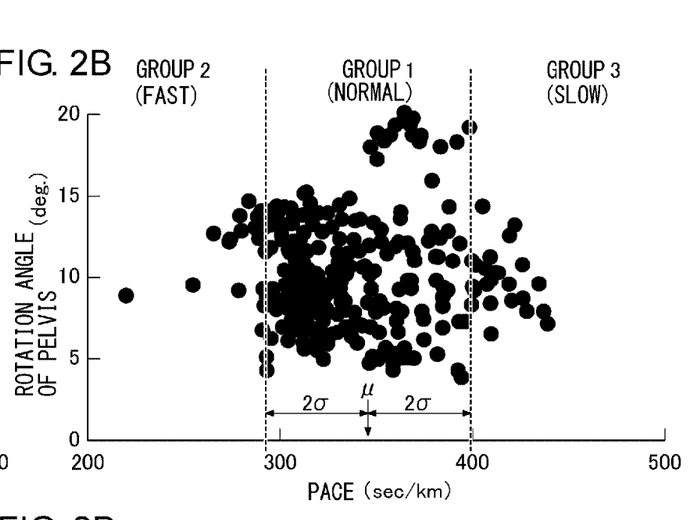

The group classification unit 120 collectively classifies the activity data recorded over a single exercise or multiple exercises by the activity data recording unit 110, into multiple groups based on the reference data. FIG. 2B shows an example of group classification for the activity data shown in FIG. 2A. In this example, assuming that the distribution of the activity data with respect to the pace as the reference data is close to a normal distribution, the activity data are classified into the following three groups, based on an average value u of the reference data in all activity data and the standard deviation o thereof.

Into a group 1, activity data of which the deviation from μ falls within +2σ are classified. If the activity data perfectly follow a normal distribution, about 95.4% of all activity data will be classified into the group 1.

Into a group 2, activity data of which the deviation from μ goes beyond −2σ are classified. If the activity data perfectly follow a normal distribution, about 2.3% of all activity data will be classified into the group 2.

Into a group 3, activity data of which the deviation from μ goes beyond +2σ are classified. If the activity data perfectly follow a normal distribution, about 2.3% of all activity data will be classified into the group 3.

The ±2σ described above is an example, and other values may also be used as a standard of the group classification. When the standard deviation o is used, as in the above example, ±kσ may be adopted as the standard width of a group, for an arbitrary positive number k. Also, although an example of classification into three groups is described above for the sake of simplicity, classification into smaller groups can also be performed. For example, classification into five groups may be performed with the four values of μ−2θ, μ−σ, μ+σ, and μ+2σ as boundaries.

The present invention is not limited to such a statistical classification method, and a boundary of each group can be set arbitrarily by the user or a computer. For example, the overall distribution of the measurement data with respect to the reference data may be approximated by a function of arbitrary dimensions, and an inflection point therein may be set as a standard of the group classification. Also, classification by supervised learning, such as regression analysis and decision trees, or clustering by unsupervised learning may be used. As the clustering method, hierarchical clustering, such as Ward's method, or non-hierarchical clustering, such as the k-means method, may be used.

In the example of FIG. 2B, the group 1 is a group in which the reference data falls within a normal range, and the groups 2 and 3 are groups in which the reference data falls outside the normal range. Since the pace is employed as the reference data here, the group 1 is constituted by activity data groups of the case where the pace is normal (about 290-400 sec/km), the group 2 is constituted by activity data groups of the case where the pace is faster than normal (less than about 290 sec/km), and the group 3 is constituted by activity data groups of the case where the pace is slower than normal (greater than about 400 sec/km). Although the majority (about 95.4%) of the activity data will belong to the group 1 of the normal range, as described previously, by forming the groups 2 and 3 separately from the group 1, the small amount (about 2.3% each) of activity data that belong to each of these groups will not be overlooked, so that appropriate exercise analysis can be performed.

Figure 2C:
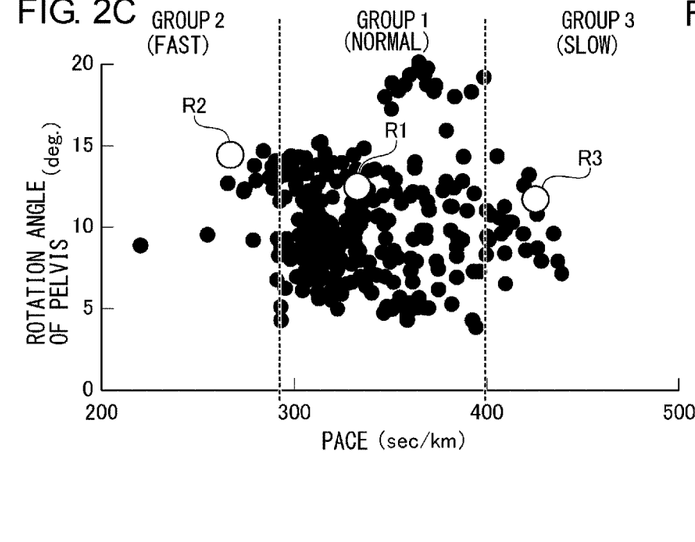

The representative data generating unit 130 generates representative data for the activity data in each group. FIG. 2C shows an example of representative data generated for the activity data shown in FIGS. 2A and 2B. Representative data R1-R3 for the respective groups 1-3 are obtained by calculating an average value of all activity data belonging to each group. More specifically, when the i-th activity data belonging to each group is represented as (xi, yi), the x coordinate of the representative data is an average value of xi, and the y coordinate of the representative data is an average value of yi. Although an average value is used here as an example of the representative data, other representative values, such as a median value and a mode value, may also be used. Also, in the group 1 of the normal range, in which a large amount of data are distributed evenly to some extent, the middle of the group width may be set to the x-coordinate of the representative data, without obtaining the average of the reference data xi.

Figure 2D:
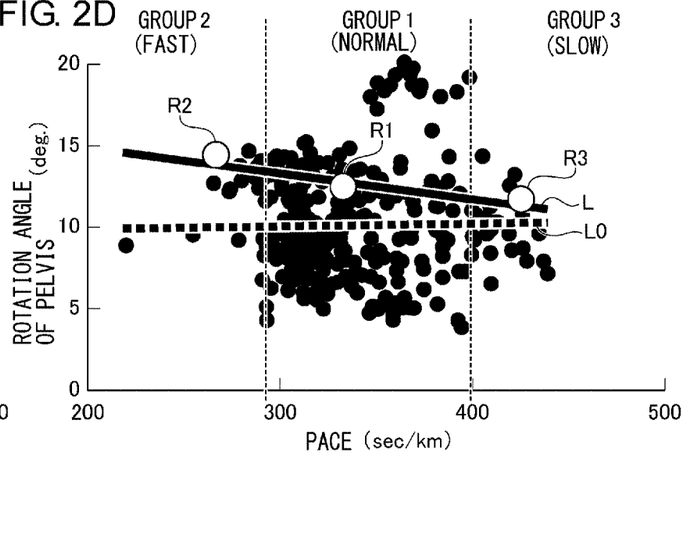

The tendency analysis unit 140 analyzes the tendency of the representative data with respect to the reference data in multiple groups. In specific, the tendency analysis unit 140 obtains a correlation established between multiple pieces of representative data and reference data. FIG. 2D shows an example of tendency analysis for the activity data shown in FIGS. 2A-2C. The tendency analysis unit 140 performs regression analysis on the representative data R1-R3 for the respective groups 1-3. The regression line L shown in FIG. 2D is a straight line representing a regression equation obtained as a result of the regression analysis.

The regression line L0 is shown as a comparative example and obtained by regression analysis performed on all activity data regardless of the groups. When the two regression lines L0 and L are compared, it can be found that the slope of the regression line L0 is almost zero and hence no particular tendency can be seen for a change in the pace as the reference data, whereas the regression line L has a negative slope and hence the rotation angle of the pelvis as the measurement data increases as the pace becomes faster from right to left in FIG. 2D. Thus, according to the present embodiment, a tendency that could not have been captured by the overall regression analysis (L0) can be captured, so that more accurate exercise analysis and guidance for improvement can be performed.

The reason why the difference as described above is made between the regression lines L0 and L is that, in the simple regression analysis for obtaining L0, the influence of the group 1, to which the majority (about 95.4%) of activity data belong, is dominant, so that the influence of the groups 2 and 3 hardly appears. In contrast, in the present embodiment, representative data for each group is first generated, and regression analysis is performed on the representative data, so that the overlook of tendencies in the groups 2 and 3, of which the amounts of data are small, can be prevented. In particular, in the analysis of an exercise such as running, disturbance in the form or unreasonable strain placed on various parts of the body often occurs when the exercise is performed outside a normal range, such as when the user runs at a faster or slower pace than usual or when the user runs for a longer or shorter distance than usual. Therefore, it is extremely important to capture the tendencies of such groups outside the normal range and to link the tendencies to the guidance for improvement.

In the above example, the regression analysis performed by the tendency analysis unit 140 is assumed to be linear regression analysis in which a regression line is obtained. Instead, nonlinear regression analysis may be performed in which a regression curve is obtained using an appropriate nonlinear model.

The guidance information generating unit 150 generates guidance information for improving exercise motions, based on the analysis performed by the tendency analysis unit 140. Although an increase in the rotation angle of the pelvis can be seen with an increase of the pace in the example of FIG. 2D, if the amount of pelvis rotation should be further increased (i.e., the absolute value of the slope of the straight line L in FIG. 2D should be further increased) in order to run faster, the guidance information for strongly encouraging the rotation of the pelvis especially when the pace is fast can be generated.

The display control unit 160 displays the analysis result from the tendency analysis unit 140 and the guidance information from the guidance information generating unit 150, on the display device 30 used by the user. When displaying the analysis result from the tendency analysis unit 140, the display control unit 160 displays the regression line L established between the multiple pieces of representative data R1-R3 and reference data. For example, the display control unit 160 displays the content of FIG. 2D as the analysis result and also displays the text of the guidance information along therewith. At the time, the regression line L0 shown as a comparative example in FIG. 2D need not be displayed. Also, only the representative data R1-R3 and the regression line L may be displayed, without displaying the points of the activity data on which the representative data R1-R3 are based.

Also, the display control unit 160 may display the analysis result from the tendency analysis unit 140 in a mode visually different for each group. For example, the color and shape of the point representing each piece of the representative data R1-R3 in FIG. 2D may be changed for each group. Also, when the points of the activity data on which the representative data R1-R3 are based are displayed, those points can be displayed in different colors and shapes for each group. Labeling each group differently, such as "normal", "fast", and "slow", as shown in FIG. 2D is also included in displaying each group in a different mode. By changing the display mode for each group in this way, advantages can be obtained such as enabling highlighting of a group that is particularly required to be improved.

Figure 3:
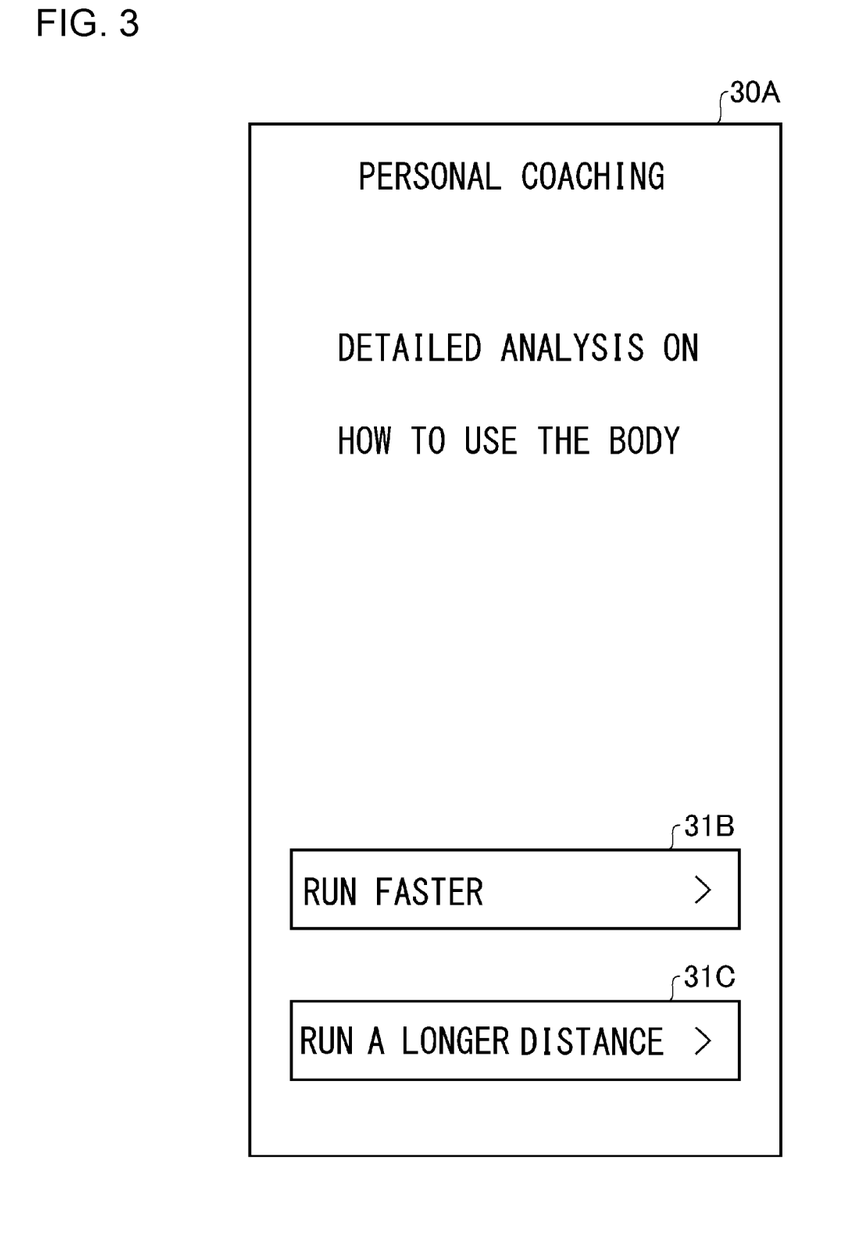
FIG. 3 is a diagram that shows an example of display of a tendency analysis result and guidance information.
Figure 4:
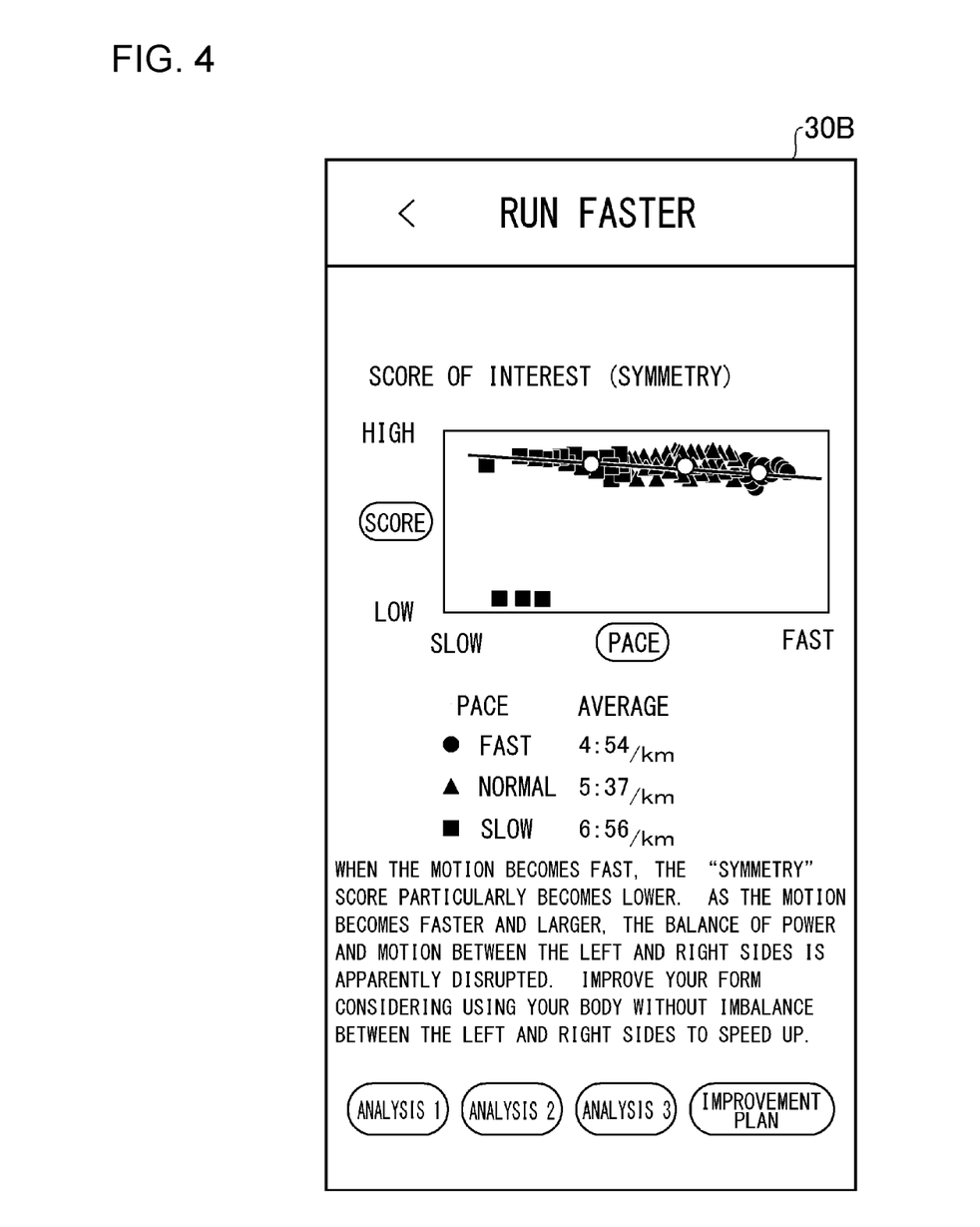
FIG. 4 is a diagram that shows another example of display of the tendency analysis result and guidance information.
Figure 5:
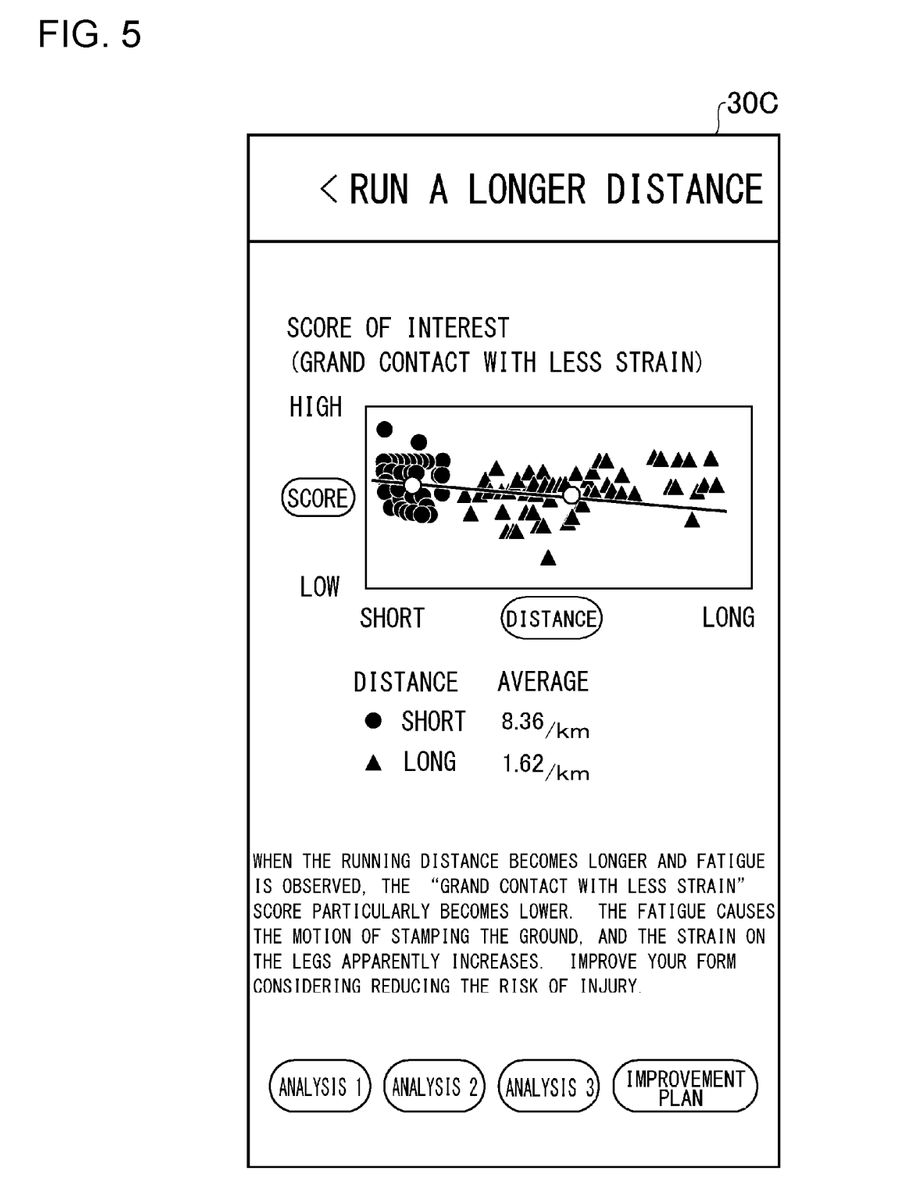
FIG. 5 is a diagram that shows yet another example of display of the tendency analysis result and guidance information.

FIGS. 3-5 show specific examples of display of the analysis result from the tendency analysis unit 140 and the guidance information from the guidance information generating unit 150. These three display examples 30A, 30B, and 30C show images displayed on the display screen of the display device 30 used by the user.

The screen 30A shown in FIG. 3 is a home screen of personal coaching on which the user obtains the analysis result and the guidance information. When the user presses two buttons 31B and 31C provided in a lower part of the screen, the screen can be shifted to the corresponding screens 30B (FIG. 4) and 30C (FIG. 5), respectively. The button 31B is labeled "RUN FASTER" and allows the user to check the result of analysis performed using the pace during running as the reference data and also check the guidance information derived therefrom, on the screen 30B after the screen shift. Also, the button 31C is labeled "RUN A LONGER DISTANCE" and allows the user to check the result of analysis performed using the distance during running as the reference data and also check the guidance information derived therefrom, on the screen 30C after the screen shift.

On an analysis result display area in an upper part of the screen 30B, to which the screen is shifted through the "RUN FASTER" button 31B, the measurement data for which a problem to be improved has been identified in the analysis performed using the pace during running as the reference data is displayed as a "score of interest". In the illustrated example, the analysis result of "symmetry" regarding the user's posture is shown as the score of interest. As in the example of FIG. 2D, activity data constituted by pairs of the reference data "pace" and the measurement data "symmetry (posture)" are classified into three groups of "slow", "normal", and "fast", based on the pace. As shown by the regression curve formed by the representative data for each group, the tendency of the "symmetry" score decreasing as the pace becomes faster can be seen.

Accordingly, on a guidance information display area in a lower part of the screen 30B, the guidance information for improvement of the score is displayed. At the bottom of the screen 30B, three buttons "ANALYSIS 1", "ANALYSIS 2", and "ANALYSIS 3" for showing the analysis result from different perspectives and an "IMPROVEMENT PLAN" button for providing more detailed guidance information are arranged. The illustrated example of "symmetry" shows the content of "ANALYSIS 1"; when "ANALYSIS 2" or "ANALYSIS 3" is pressed, the analysis result and guidance information regarding measurement data other than symmetry, such as the "rotation angle of the pelvis" shown in FIG. 2D, is displayed. In this way, with respect to the same reference data "pace", the analysis result and guidance information for different measurement data can be displayed, so that the user can improve the exercise motions from various perspectives.

On the analysis result display area in an upper part of the screen 30C, to which the screen is shifted through the "RUN A LONGER DISTANCE" button 31C, the measurement data for which a problem to be improved has been identified in the analysis performed using the distance during running as the reference data is displayed as the "score of interest". In the illustrated example, the analysis result of "grand contact with less strain" regarding the landing impact is shown as the score of interest. As in the example of FIG. 2D, activity data constituted by pairs of the reference data "distance" and the measurement data "grand contact with less strain (landing impact)" are classified into two groups of "short" and "long", based on the distance. In the illustrated example, the area of around medium distance located in the center of the graph is also classified into the group "long", because no significant difference between these medium and long distance areas can be found in the score of interest and hence the areas can be treated as the same group. Thus, the group classification unit 120 of the present embodiment can perform optimal group classification for exercise analysis, with reference to the tendency of the activity data.

As shown by the regression line formed by the representative data for these two groups, the tendency of the "grand contact with less strain" score decreasing as the distance becomes longer can be seen. Accordingly, on the guidance information display area in a lower part of the screen 30C, the guidance information for improvement of the score is displayed. As in the screen 30B, at the bottom of the screen 30C, the three buttons "ANALYSIS 1", "ANALYSIS 2", and "ANALYSIS 3" for showing the analysis result from different perspectives and the "IMPROVEMENT PLAN" button for providing more detailed guidance information are arranged.

Through the display screens described above, the user can obtain the analysis results for various reference data, such as the "pace" and "distance", and can also obtain appropriate advice on items that are required to be improved, such as the "symmetry", "rotation angle of the pelvis", and "grand contact with less strain".

Figure 6:
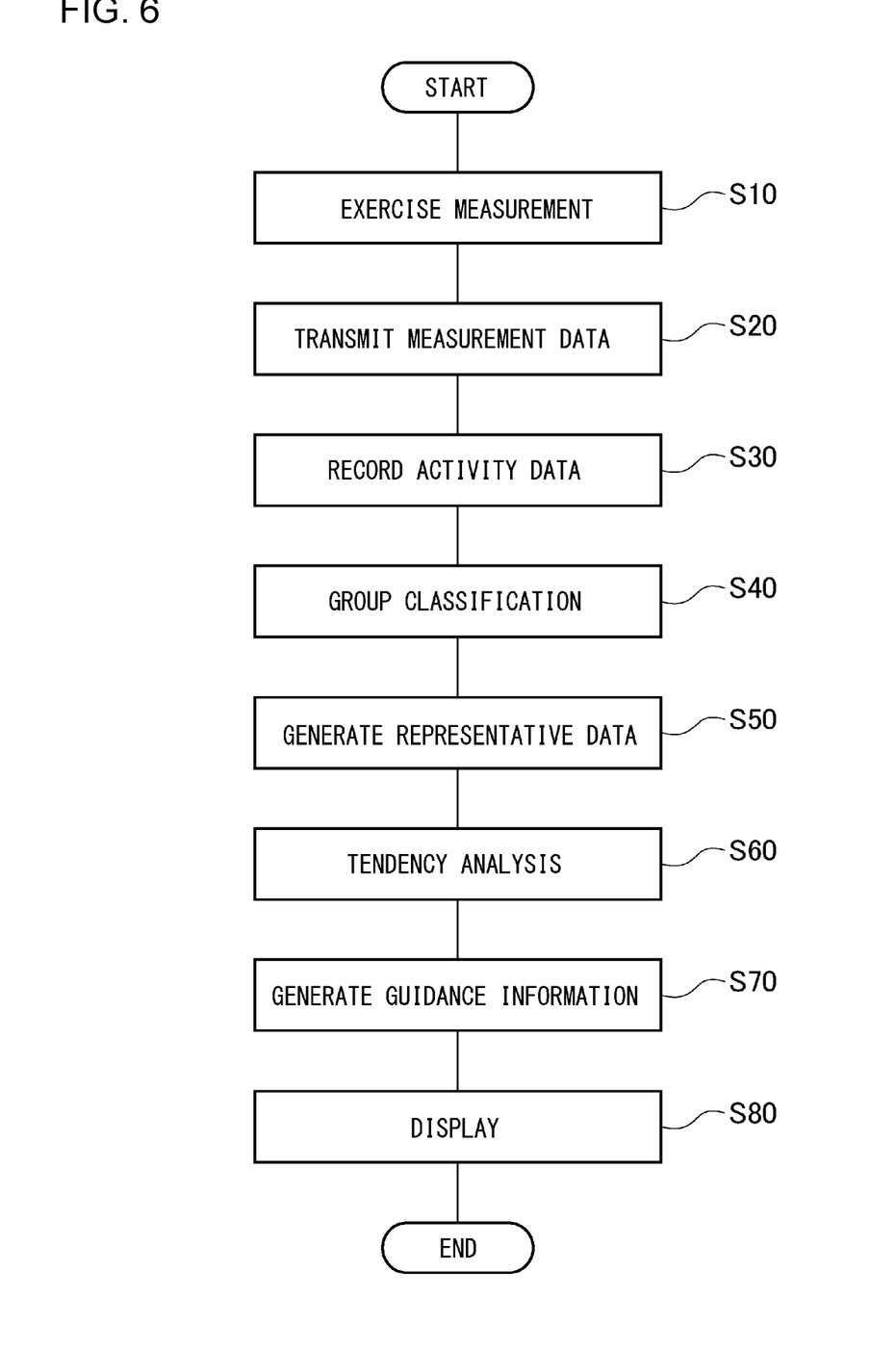
FIG. 6 is a flow diagram of exercise analysis processing performed by the exercise analysis device.

FIG. 6 shows the flow of exercise analysis processing performed by the exercise analysis device 100 as described above. In the following description, "S" means a step.

At S10, measurement by the measurement device 20 is performed during a user's exercise. As described previously, the measurement device 20 measures both the measurement data associated with an exercise motion and the reference data used as a standard in the group classification performed by the group classification unit 120.

At S20, the measurement device 20 transmits the measurement data (the measurement data associated with an exercise motion and the reference data) to the exercise analysis device 100. At the time, when the exercise measurement at S10 is performed using multiple measurement devices 20, the measurement data from all the measurement devices 20 are transmitted to the exercise analysis device 100. Also, when multiple pieces of data are measured using a single measurement device 20, all the measurement data are transmitted to the exercise analysis device 100.

At S30, the activity data recording unit 110 records, as activity data, the measurement data associated with an exercise motion and the reference data related to each other (FIG. 2A). At S30, the activity data over a single exercise or multiple times of exercises can be recorded.

At S40, the group classification unit 120 classifies the activity data recorded over a single exercise or multiple times of exercises at S30, into multiple groups based on the reference data (FIG. 2B).

At S50, the representative data generating unit 130 generates representative data for the activity data in each group (FIG. 2C).

At S60, the tendency analysis unit 140 analyzes a correlation of the representative data with respect to the reference data in multiple groups and obtains a relational expression established between the multiple pieces of representative data and reference data (FIG. 2D).

At S70, the guidance information generating unit 150 generates guidance information for improving exercise motions, based on the tendency analysis performed at S60.

At S80, the display control unit 160 transmits, to the display device 30 used by the user, and displays, on the display screen thereof, the tendency analysis result obtained at S60 and the guidance information generated at S70 (FIGS. 3-5).

The present embodiment has been described in line with the configuration thereof. In addition to the above described, the present embodiment also provides the following functions and effects, for example.

In the present embodiment, by classifying a series of activity data recorded during exercise into multiple groups and by analyzing the tendency of the representative data among the groups, the exercise motions can be appropriately analyzed in consideration of the tendency of the entire exercise, and the guidance information for improving the exercise motions can be generated.

In the present embodiment, since exercise analysis can be performed based on the activity data recorded over a single exercise or multiple exercises, a point to be improved that appears constantly throughout the recording period can be effectively discovered, and appropriate guidance for improvement can be provided.

Also, with the regression curve L generated by the tendency analysis unit 140 in the present embodiment, not only can the tendency of a group with a small amount of data be appropriately grasped, but even an area where no data exist yet can be estimated ahead, which can be utilized for goal setting and exercise guidance in consideration thereof. For example, when the goal in terms of distance is set to completion of a full marathon of 42.195 km, even if the current maximum running distance is 30 km, using the regression curve L can estimate the measurement data in the range of 30 km to 42.195 km, which have not yet been run. Accordingly, a problem deduced from the measurement data can be extracted, and the exercise guidance for solving the problem before it arises can be provided. Also, in order to complete a full marathon in the target time of 4 hours, for example, it is necessary to run 1 km at a pace faster than 5 minutes. If there is no data or significantly less data for such a faster pace at present, it may be recommended to practice at a faster pace to achieve the goal. At the time, using the regression curve L regarding the pace, as with that regarding the distance described above, even if there is no data in a fast-pace area, a deduced problem can be extracted, and the exercise guidance can be provided.

The present invention has been described based on an embodiment. The embodiment is intended to be illustrative only, and it will be obvious to those skilled in the art that various modifications to a combination of constituting elements or processes could be developed and that such modifications also fall within the scope of the present invention.

Although the pace is used as the reference data for the group classification in the present embodiment, one or more reference data other than the pace may also be used. As cited in the present embodiment, time, the number of steps, distance, positions, speed, acceleration, altitude, gradients, luminance, temperature, humidity, and biological signals such as heartbeat may be used as the reference data, for example. For example, when altitude information or gradient information is used as the reference data, a problem that appears in exercise motions at a specific altitude or gradient can be effectively found. Also, when biological signals such as heartbeat is used as the reference data, a problem that appears in exercise motions depending on the user's physical condition can be effectively found. Furthermore, when multiple reference data are used, an essential problem can be found from multiple perspectives as described above.

Although the group classification in the present embodiment is performed by the group classification unit 120 based on statistical values such as the average value u and the standard deviation o, the group classification may be performed without using statistical values. For example, in FIG. 2B, groups may be configured by dividing the area into uniform predetermined widths, such as 100 sec/km.

The present embodiment has been described employing running as an example of the exercise. However, the present invention is also applicable to other exercises. For example, it is applicable to various athletics, swimming, gymnastics, training and exercises for road biking or the like, dance, and ball sports such as soccer.

The functional configuration of each device described in the embodiment can be implemented by hardware resources, software resources, or cooperation between hardware resources and software resources. As the hardware resources, processors, ROMs, RAMs, or other LSIs can be employed. As the software resources, programs, such as operating system programs and application programs, and cloud services or other services can be employed.

REFERENCE SIGNS LIST 100 exercise analysis device
110 activity data recording unit
120 group classification unit
130 representative data generating unit
140 tendency analysis unit
150 guidance information generating unit
160 display control unit
20 measurement device
30 display device

INDUSTRIAL APPLICABILITY

The present invention relates to an exercise analysis device that analyzes exercise motions.

The invention claimed is:

1. An exercise analysis device, comprising:
a group classification unit that classifies activity data, as which measurement data of a posture or a rotation angle of waist or pelvis of a user is recorded together with predetermined reference data that changes during exercise, into a plurality of groups based on the reference data;
a representative data generating unit that generates representative data for the activity data in each of the plurality of groups; and
a tendency analysis unit that analyzes a tendency of the representative data with respect to the reference data in the plurality of groups,
wherein the group classification unit is configured to classify the activity data based on an average value of the predetermined reference data and a standard deviation of the activity data,
the representative data generating unit is configured to generate the representative data by calculating an average value of the activity data belonging to each of the plurality of groups, and
the tendency analysis unit is configured to perform regression analysis on the representative data of the plurality of groups.

2. The exercise analysis device according to claim 1, wherein the plurality of groups include a group of which the reference data falls within a normal range, and a group of which the reference data falls outside the normal range.

3. The exercise analysis device according to claim 1, wherein the tendency analysis unit performs the regression analysis by obtaining a relational expression established between a plurality of pieces of the representative data and the reference data.

4. The exercise analysis device according to claim 1, wherein the group classification unit classifies the activity data recorded over a plurality of exercises into the groups.

5. The exercise analysis device according to claim 1, further comprising a guidance information generating unit that generates guidance information for improvement of an exercise motion, based on analysis performed by the tendency analysis unit.

6. The exercise analysis device according to claim 1, further comprising a display control unit that displays an analysis result from the tendency analysis unit.

7. The exercise analysis device according to claim 6, wherein the display control unit displays a relational expression established between a plurality of pieces of representative data and the reference data.

8. The exercise analysis device according to claim 6, wherein the display control unit displays an analysis result from the tendency analysis unit in a mode visually different for each of the groups.

9. An exercise analysis method, comprising:
a group classification step of classifying activity data, as which measurement data of a posture or a rotation angle of waist or pelvis of a user is recorded together with predetermined reference data that changes during exercise, into a plurality of groups based on the reference data;
a representative data generating step of generating representative data for the activity data in each of the plurality of groups; and
a tendency analysis step of analyzing a tendency of the representative data with respect to the reference data in the plurality of groups,
wherein the group classification step classifies the activity data based on an average value of the predetermined reference data and a standard deviation of the activity data,
the representative data generating step generates the representative data by calculating an average value of the activity data belonging to each of the plurality of groups, and
the tendency analysis step performs regression analysis on the representative data of the plurality of groups.

10. A computer-readable medium storing an exercise analysis program causing a computer to implement:
a group classification step of classifying activity data, as which measurement data of a posture or a rotation angle of waist or pelvis of a user is recorded together with predetermined reference data that changes during exercise, into a plurality of groups based on the reference data;
a representative data generating step of generating representative data for the activity data in each of the plurality of groups; and
a tendency analysis step of analyzing a tendency of the representative data with respect to the reference data in the plurality of groups,
wherein the group classification step classifies the activity data based on an average value of the predetermined reference data and a standard deviation of the activity data, the representative data generating step generates the representative data by calculating an average value of the activity data belonging to each of the plurality of groups, and the tendency analysis step performs regression analysis on the representative data of the plurality of groups.

\* \* \* \* \*